United States Patent
Della Valle et al.

(10) Patent No.: US 12,364,678 B2
(45) Date of Patent: *Jul. 22, 2025

(54) PHARMACEUTICAL COMPOSITION COMPRISING PALMITOYLETHANOLAMIDE AND L-ACETYLCARNITINE

(71) Applicant: EPITECH GROUP S.P.A., Milan (IT)

(72) Inventors: Francesco Della Valle, Milan (IT); Maria Federica Della Valle, Milan (IT)

(73) Assignee: Epitech Group S.P.A., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 18/184,797

(22) Filed: Mar. 16, 2023

(65) Prior Publication Data

US 2023/0285349 A1 Sep. 14, 2023

Related U.S. Application Data

(63) Continuation of application No. 16/436,143, filed on Jun. 10, 2019, now abandoned, which is a
(Continued)

(30) Foreign Application Priority Data

Mar. 19, 2014 (IT) .......................... MI2014A000454

(51) Int. Cl.
*A61K 31/221* (2006.01)
*A61K 9/00* (2006.01)
(Continued)

(52) U.S. Cl.
CPC .......... *A61K 31/221* (2013.01); *A61K 9/0024* (2013.01); *A61K 9/1647* (2013.01); *A61K 31/164* (2013.01); *A61K 31/7034* (2013.01)

(58) Field of Classification Search
None
See application file for complete search history.

(56) References Cited

U.S. PATENT DOCUMENTS 5,679,667 A * 10/1997 Della Valle .......... A61K 31/164
514/354
5,973,004 A 10/1999 Howard
(Continued)

FOREIGN PATENT DOCUMENTS

WO 2011/027373 3/2011

OTHER PUBLICATIONS

Clayton. Int. J. Mol. Sci. 2021, 22, 5305.*
(Continued)

*Primary Examiner* — Nicole P Babson
*Assistant Examiner* — Lori K Mattison
(74) *Attorney, Agent, or Firm* — Dunlap Bennett & Ludwig (57) ABSTRACT

It is the object of the present invention a pharmaceutical composition for use in humans or animals containing N-palmitoylethanolamide for the control of the inflammatory and/or neuropathic pain of various origin. In particular, the present invention relates to a pharmaceutical composition comprising palmitoylethanolamide (PEA and L-acetylcarnitine (LAC), optionally with in addition an antioxidant compound such as a polyphenol, alpha-lipoic acid, and L-acetylcysteine.

7 Claims, 6 Drawing Sheets

Related U.S. Application Data continuation-in-part of application No. 15/603,566, filed on May 24, 2017, now Pat. No. 10,441,559, which is a continuation of application No. 14/658,369, filed on Mar. 16, 2015, now abandoned.

(51) Int. Cl.
*A61K 9/16* (2006.01)
*A61K 31/164* (2006.01)
*A61K 31/7034* (2006.01)
*A61K 9/08* (2006.01)

(56) References Cited

U.S. PATENT DOCUMENTS

| | | | |
|---|---|---|---|
| 5,990,170 A | 11/1999 | Della Valle et al. | |
| 6,365,622 B1* | 4/2002 | Cavazza | A61K 31/385 514/556 |
| 6,470,373 B1 | 10/2002 | Moller | |
| 6,548,550 B1 | 4/2003 | Cornelli et al. | |
| 8,663,701 B2 | 3/2014 | Della Valle et al. | |
| 2004/0247633 A1* | 12/2004 | Eberl | A61K 8/442 514/502 |
| 2005/0065216 A1* | 3/2005 | Bisogno | A61K 31/00 514/630 |
| 2006/0093629 A1* | 5/2006 | Buehler | A61K 47/36 424/400 |
| 2011/0171313 A1 | 7/2011 | Della Valle et al. | |

OTHER PUBLICATIONS

Chaumeil. Methods and Findings in Experimental and Clinical Pharmacology. 1998; 20(3): 211-215.*
Walpole. BMC Public Health 2012, 12:439.*
Ardizzone, Effect of Ultra-Micronized-Paimitoylethanolamide and Acetyl-L-Carnitine on Experimental Model of Inflammatory Pain. Int. J. Mol Sci. 2021, 22,967.
Slinker, J. Mol. Cell. Cardiol 30, 723-731 (1998).
Chiechio et al. L.-Acetylcanitine: A Proposed Therapeutic Agent for Painful Peripheral Neuropathies. Current Neuropharmacology, vol. 4, No. 3, Jul. 1, 2006, pp. 235-237.
Chiechio et al. Acetyl-L-Carnitine in Neuropathic Pain. CNS Drugs, Adis International, Auckland, NZ, vol. 21,, No. suppl. 1, Jan. 1, 2007, pp. 31-38.
Gattiantonio et al. Palmiloylethanolamide in the Treatment of Chronic Pain Caused by Different Etiopathogenesis. Pain Medicine, Sep. 2012, vol. 13, No. 9, pp. 1121-1130.
Hesselink et al. New Targets in Pain, Non-Neuronal Cells, and the Role of Palmitoylethanolamide. Open Pain Journal 2012, Bentham Science Publishers B.V. NLD, vol. 5, No., May 2010, pp. 76-79.
Indraccolo U et al. Effect o fPalmitoylethanoloamide-polydatin Combination of Chronic Pelvic Pain Associated with Endometriosis: Preliminary Observations, European Journal of Obstetrics & Gynecology and Reproductive Biology. Excerpta Medica, Amsterdam, NL. vol. 150, No. 1, May 2010, pp. 76-79.
Gilron et al. Morphine, Gabapentine, or Their Combination of Neuropathatic Pain, The New England Journal of Medicine, 352;13, Mar. 31, 2005, pp. 1324-1334.
Gilron et al. Nortriptyline and gabapentin, alone and in combination for neuropathic pain: a double-blind, randomized controlled cross-over trial. THe Lancet, vol. 374, Oct. 10, 2009, pp. 1252-1261.
Sima et al. Acetyl-L-Carnitine Improves Pain, Nerve Regeneration, and Vibratory Perception in Patients with Chronic Diabetic Neuropathy. Diabetes Care, vol. 28, No. 1, Jan. 1, 2005, pp. 89-94.
Vorobeychik et al. Combination Therapy for Neuropathic Pain CNS Drugs, vol. 25, issue 12, Dec. 2011, pp. 1023-1034.
Teede et al. Neuropathic Pain: Redefinition and a grading system or clinical research purposed. Neurology, vol. 70, 208, pp. 1630-1635.
Bennet and Xie. Pain, 1998, 33:87-107.
Hargreaves et al Pain, 1988, 32, 77-68.

* cited by examiner

| | Control/vehicle | CCI/vehicle | CCI/LAC 100mg/kg | CCI/LAC 10mg/kg | CCI/PEA-um 10mg/kg | CCI/PEA-um 5mg/kg | CCI/PEA-um 5mg/kg /LAC10mg/kg | CCI/PEA 5mg/kg co-micronized with polydetina 0,5 mg/kg /LAC 10 mg/kg |
|---|---|---|---|---|---|---|---|---|
| Day 0 | 5,0 | 5,0 | 5,0 | 5,0 | 5,0 | 5,0 | 5,0 | 5,0 |
| Day 4 | 4,9 | 1,3 | 2,8 | 1,4 | 3,5 | 1,8 | 4,0 | 4,6 |
| Day 8 | 4,9 | 1,2 | 3,3 | 1,7 | 4,0 | 2,2 | 4,4 | 4,8 |

FIG. 1

Results a) paw volume (ml)

| Time | SHAM | LAC 5mg/kg | PEA-m 5mg/kg | LAC 2,5mg/kg + PEA-m 2,5mg/kg |
|---|---|---|---|---|
| 30 min | 0,50 | 0,50 | 0,50 | 0,50 |
| 1 h | 0,75 | 0,75 | 0,75 | 0,65 |
| 2 h | 1,75 | 1,75 | 1,73 | 1,48 |
| 3 h | 2,25 | 2,00 | 1,95 | 1,65 |
| 4 h | 2,25 | 2,00 | 1,98 | 1,35 |
| 5 h | 2,35 | 2,20 | 2,20 | 1,10 |
| 6 h | 2,45 | 2,2 | 2,18 | 1,05 |

FIG. 2A b) mechanical hyperalgesia
paw withdrawal latency (seconds)

| Time | SHAM | LAC 5mg/kg | PEA-m 5mg/kg | LAC 2,5mg/kg + PEA-m 2,5mg/kg |
|---|---|---|---|---|
| 30 min | 14,8 | 14,8 | 14,8 | 14,8 |
| 1 h | 11,0 | 11,0 | 11,0 | 12,0 |
| 2 h | 7,5 | 7,5 | 7,5 | 9,0 |
| 3 h | 7,5 | 7,5 | 7,5 | 12,0 |
| 4 h | 6,5 | 7,0 | 7,2 | 11,0 |
| 5 h | 6,0 | 6,0 | 6,2 | 11,0 |
| 6 h | 6,0 | 5,8 | 6,0 | 10,0 |

PHARMACEUTICAL COMPOSITION COMPRISING PALMITOYLETHANOLAMIDE AND L-ACETYLCARNITINE

CROSS REFERENCE TO RELATED APPLICATIONS

This application is a Continuation-in-Part of U.S. application Ser. No. 15/603,566, filed May 24, 2017, which is a Continuation of U.S. application Ser. No. 14/658,369, filed Mar. 16, 2015, which claims priority from Italian Patent Application Serial No. MI2014A000454, filed Mar. 19, 2014; the disclosure of each of which is incorporated herein by reference in its entirety

TECHNICAL FIELD OF THE INVENTION

The object of the present invention is a pharmaceutical composition for use in humans or animals containing N-palmitoylethanolamide for controlling the inflammatory and/or neuropathic pain of various origin.

BACKGROUND

Today, neurogenic pain, also referred to as inflammatory pain, can be defined as the consequence of a complex multi-factorial mechanism localized in the innervated tissues and/or in the miniaturized endoneurial compartment in which, in addition to the nociceptive nerve terminals and/or the axons composing the peripheral sensitive fibers, the endothelial cells of the microcirculation, both tissue and endoneurial mastocytes, and cells of an immunologic nature extravasated from the tissue microcirculation in cases of suffering of the peripheral nervous system and/or of the tissue it innervates are involved. The whole process is defined as neurogenic inflammation, and it gives rise to the phenomenon referred to as peripheral sensitization.

The neuropathic pain, characteristic of neuropathies caused by traumatic, compressive, dysmetabolic, and infective injuries, is characterized by spontaneous pain, allodynia, and hyperalgesia. Today, the "central sensitization" found at the level of the dorsal horns of the spinal cord, generally as a consequence of a lesion or an alteration of the somato-sensory nervous system (Neurology 2008; 70:1630-1635), is recognized as the most important mechanism on which of chronic pain is based. In addition to the synaptic junction between the first and second neuron, glial cells and in particular the microglia are involved in this sensitization process. The activation and proliferation of the microglia induced, as stated above, by an injury or dysmetabolism of neuronal systems (peripheral, spinal, supraspinal) results in a significant alteration of the synaptic plasticity induced by growth factors of protein origin released by the microglia, with a substantial modification of the neurotransmission (peptidergic, glutamatergic) dialogue between the first and second neurons. In particular, the neurotransmission at the level of said synaptic junction is deeply changed, passing from an essentially glutamatergic neurotransmission through NMDA-type receptors to a mixed neurotransmission, glutamatergic—in part still of an NMDA type and in part of a metabotropic type (through a series of glutamatergic receptors belonging to the mGlu family)—and peptidergic, essentially related to the neuropeptide knowns as Substance P (SP).

It is known that palmitoylethanolamide, an endogenous lipid of an N-acylethanolamide nature produced on demand in the case of a cell damage, is capable of modulating in an inhibitory manner both the hyper-degranulation of the mastocyte and the hyper-activation of the microglia, thus showing to be capable, when administered in such a pharmaceutical form as to ensure bioavailability at the level of the above-mentioned two target cells, of controlling the neuronal—peripheral and central—sensitization and, consequently, both the inflammatory and neuropathic pain. In particular, palmitoylethanolamide showed a particularly relevant effect, at the dose of 10 mg/kg, in the neuropathic pain model obtained by sciatic nerve ligation in the mouse; clinically, many studies proved the ability of palmitoylethanolamide, administered p.o. in an appropriate form—e.g., micronized and/or ultramicronized—of reducing both inflammatory pain and chronic and neuropathic pain associated with several disease conditions.

L-Acetylcarnitine (LAC), a molecule which is typically used in the treatment of painful neuropathies, proved to be able, at a dose of 100 mg/kg, to decrease the mechanical allodynia in the neuropathic pain model obtained by sciatic nerve ligation in rodents (CCI). The mechanism of action of such molecule is a selective over-regulation of the metabotropic receptors for glutamate, and in particular of the receptor referred to as mGlu2 at the level of the joint between the first and the second neurons, located in the posterior horns of the spinal cord.

SUMMARY OF THE INVENTION

The inventors of the present patent have surprisingly found that the association between palmitoylethanolamide, in any form and particularly in micronized or ultramicronized form, and L-acetylcarnitine is capable of providing a highly synergic effect between the two molecules, which effect is particularly clear on neuropathic pain.

They have further found that the addition of a molecule with antioxidative activity to the association between palmitoylethanolamide and L-acetylcarnitine—optionally co-micronized with palmitoylethanolamide—further enhances the synergy between the two main components of the invention.

A further important evidence is that the composition of the invention, when administered to a subject in comparison with a separate administration of palmitoylethanolamide and L-acetylcarnitine (e.g. a combination therapy), displayed an improved effect in challenging inflammatory conditions, in particular painful conditions.

Therefore, an object of the present invention is a pharmaceutical composition comprising palmitoylethanolamide (PEA), alternatively in non-micronized form (non-micronized PEA), or in micronized form (PEA-m), or in ultra-micronized form (PEA-um), and L-acetylcarnitine in finely pulverized form.

A further object of the invention is a pharmaceutical composition comprising palmitoylethanolamide (PEA) as defined above, L-acetylcarnitine, and antioxidative molecules of the polyphenols family (e.g., polydatin, resveratrol, luteolin, quercetin, rutin, etc.), α-lipoic acid, and/or acetylcysteine.

The invention is defined by the appended claims. Further characteristics and advantages of the process according to the invention will be apparent from the description set forth below of preferred embodiments, given by way of illustrative, non-limiting examples.

DETAILED DESCRIPTION OF THE INVENTION

The invention relates to a pharmaceutical composition comprising palmitoylethanolamide (PEA), alternatively in non-micronized form (non-micronized PEA), or in micronized form (PEA-m), or in ultra-micronized form (PEA-um), and L-acetylcarnitine in finely pulverized form.

Palmitoylethanolamide can be synthetized as described in Example no. 25 of U.S. Pat. No. 5,990,170.

Non-micronized PEA can be obtained by finely grounding the product from the synthesis; a product with a particle size ranging between 50.0 and 100.0 µm can be obtained.

PEA-m can be obtained as described in the U.S. Pat. No. 6,548,550 B1 and it has a particle size ranging between 2.0 and 10.0 µm.

PEA-um can be obtained as described in the patent application PCT issued with no. WO 2011/027373 A1 and it has a particle size ranging between 0.8 and 6.0 µm.

More indications on said forms of PEA are present in the above-mentioned patent publications, the content of which relating to the characterization of the product is incorporated herein by reference.

It should be understood that, when a range of particle size is indicated, this defines the range wherein the peak of the particle size distribution curve is positioned, as it is known to the expert in the field. Normal grinding methods as well as micronization or ultra-micronization methods do not in fact result in a sharp particle size distribution peak. A Gaussian-like curve is instead displayed, wherein a certain percentage of particles have a size below or above the given range (see for example European Pharmacopoeia 8.0, Section 2.9.35, Table 2.9.35-1).

Pharmaceutical grade L-acetylcarnitine is a commercially available product.

The pharmaceutical composition of the invention comprises palmitoylethanolamide in weight percentages ranging between 20 and 35%, L-acetylcarnitine in weight percentages between 20 and 55%, and one or more compounds with antioxidant activity in total weight percentages ranging between 0 and 20%.

The compound with antioxidant activity is preferably selected from the group comprising polyphenols, alphalipoic acid (or thioctic acid), and the L-acetylcysteine.

When the antioxidant compound is or comprises a polyphenol, it is preferably selected from polydatin, resveratrol, luteolin, quercetin and rutin.

The molecules having an antioxidative activity may also be co-micronized with palmitoylethanolamide according to the teachings described in U.S. Pat. No. 6,548,550 B1.

The antioxidative compounds are commercially available products.

The inventive composition can further contain pharmaceutically acceptable excipients and additives, selected as a function of the desired pharmaceutical form.

The diseases which can be treated with the composition object of the present invention comprise:
- Both acute and chronic painful peripheral neuropathies of dysmetabolic, compressive, traumatic, toxic, infectious, iatrogenic origin;
- Pain associated with vertebral column and spinal cord diseases of traumatic, dysmetabolic, degenerative, infectious, iatrogenic origin;
- Pain associated with small fibre diseases of infectious, traumatic, dysmetabolic, iatrogenic origin;
- Acute and/or chronic pain associated with diseases in the pelvic area, such as Endometriosis, Interstitial Cystitis, Recurrent Cystitis, Irritable Bowel Syndrome, Prostatitis, Vaginitis, Vulvovaginitis, primary and secondary Dysmenorrhea, Vulvodynia, Vestibulodynia;
- Pain associated with traumatic and degenerative joint diseases;
- Pain associated with arthritic diseases.

The pharmaceutical composition according to the present invention can be formulated for an oral, buccal, or rectal administration.

For the oral administration, the pharmaceutical compositions can be, for example, in the form of tablets or capsules prepared in a conventional manner with pharmaceutically acceptable excipients, such as binders (e.g., pre-gelatinized corn starch, polyvinylpyrrolidone, or hydroxypropyl methylcellulose); filling agents (e.g., lactose, microcrystalline cellulose or calcium hydrogen phosphate); lubricants (e.g., magnesium stearate, talc, or silica); disintegrating agents (e.g., potato starch or sodium starch glycolate); or inhibiting agents (e.g., sodium lauryl sulfate). The tablets can be coated by methods well known in the art. The liquid preparations for oral administration can be, for example, in the form of solutions, syrups or suspensions, or they can be in the form of lyophilized products to be reconstituted, before their use, with water or other suitable vehicles. Such liquid preparations can be prepared by conventional methods with pharmaceutically acceptable additives, such as suspending agents (e.g., sorbitol syrup, cellulose derivatives, or edible hydrogenated fats); emulsifying agents (e.g., lecithin or acacia); non-aqueous vehicles (e.g., almond oil, oily esters, ethyl alcohol, or fractionated plant-based oils); and preservatives (e.g., methyl- or propyl-p-hydroxybenzoates or sorbic acid). The preparation may also suitably contain flavors, colorants, and sweeteners.

The preparations for oral administration can be suitably formulated to allow the controlled release of the active ingredient.

For the buccal administration, the compositions can be in the form of tablets or lozenges formulated in a conventional manner, suitable for an absorption by the buccal mucosae. Typical buccal formulations are the tablets for sub-lingual administration.

According to the present invention, the compounds can also be formulated in rectal compositions, such as suppositories or retention enema, for example containing the base components of typical suppositories, such as cocoa butter or other glycerides.

In addition to the compositions described above, the compounds can also be formulated as depot preparations. Such long-acting formulations can be administered by an implant (for example, subcutaneously, transdermally, or intramuscularly) or by intramuscular injection. Thus, for example, the compounds, according to the present invention, can be formulated with suitable polymeric or hydrophobic materials (e.g., in the form of an emulsion in a suitable oil) or ionic exchange resins, or as minimally soluble derivatives, for example, as a minimally soluble salt.

According to the present invention the dose of the compounds proposed for the administration to a human being (with a body weight of about 70 Kg) ranges from 10 mg to 1 g, and preferably from 100 mg to 500 mg of the active ingredients per dose unit. The dose unit can be administered, for example, 1 to 4 times/day. The dose will depend on the selected administration route. It shall be considered that it could be necessary to continuously vary the dosage as a function of the age and weight of the patient, and also of the severity of the clinical condition to be treated. Finally, the precise dose and the administration route will be at discretion of the attending physician or veterinary.

The formulations described above can be prepared according to conventional methods, such as those described in Remington's Pharmaceutical Sciences Handbook, Mack Pub. Co., N.Y., USA.

EXPERIMENTAL SECTION

Experimental Model of Neuropathic Pain

The experiments were carried out by using male mice of the C57BL/6J strain with a weight ranging between 25 and 30 g; 10 animals per group were used. The animals were anesthetized with sodium pentobarbital (60 mg/kg, i.p.) and subjected to a surgical procedure of sciatic nerve ligation capable of inducing neuropathic pain in accordance with the method described by Bennet and Xie (1988, Pain; 33:87-107). Sham animals were used as a control.

The products were administered p.o. with a tube, suspended in 2% CarboxymethylCellulose.

The mechanical allodynia was measured by using the Dynamic Plantar Aesthesiometer equipment of the Company Ugo Basile-Varese, Italy.

Figure 1:
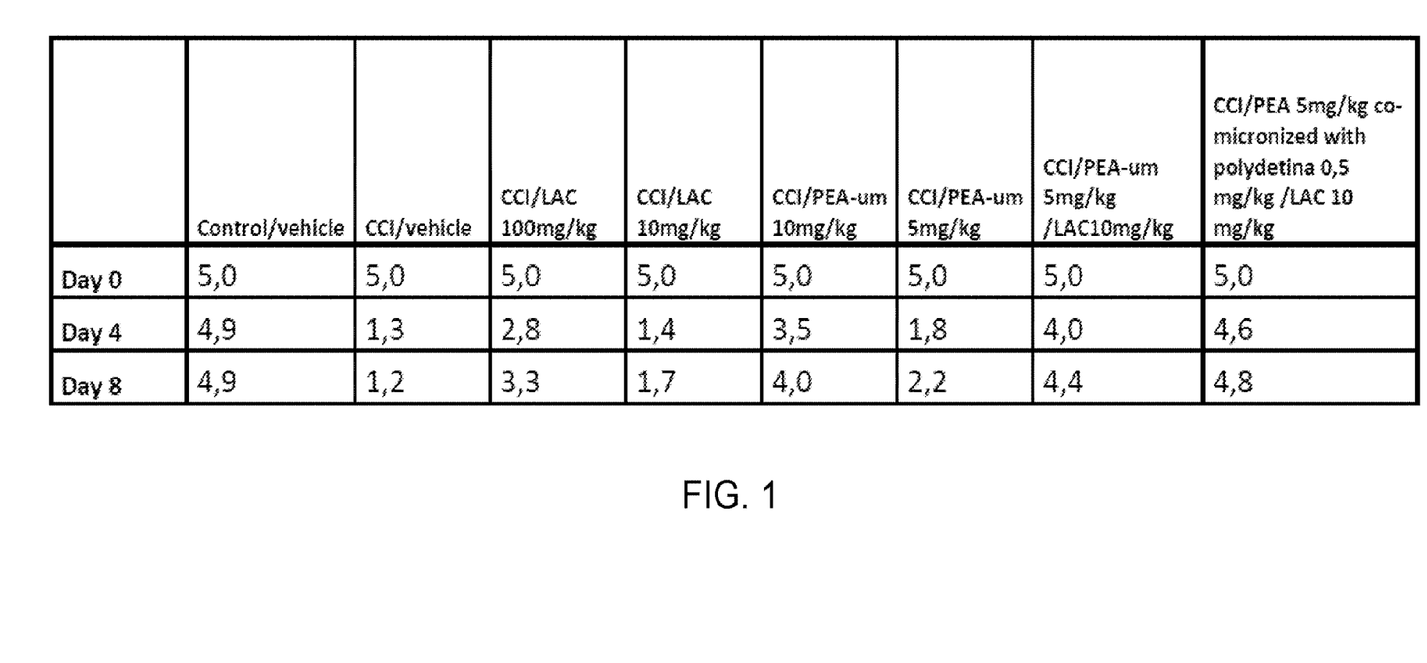
FIG. 1 shows a Table illustrating the data regarding a mechanical allodynia test following a sciatic nerve ligation in mouse, wherein ultra-micronized PEA is used.

Data are set forth in Table of FIG. 1. The values in the table are referred to the weight, expressed in grams, to which the animal object of the experiment, subjected thereto, withdraws its paw when feeling pain.

It is pointed out from the data set forth in the table that LAC alone or PEA-um alone cause a significant alleviation of the neuropathic pain when used at doses, of 100 mg/kg and 10 mg/kg, respectively, while, at a dose of 10 mg/kg for LAC alone and of 5 mg/kg for PEA-um alone, the two substances do not cause a significant activity.

Vice versa, PEA-um at a dose from 5 mg/kg in association with LAC at a dose of 10 mg/kg, causes a very high decrease of the neuropathic pain after 8 days of treatment.

Finally, the association of PEA (5 mg/kg) co-micronized with polydatin (0.5 mg/kg) and in association with LAC (10 mg/kg) cause an almost complete remission of neuropathic pain after 8 days of treatment.

Therefore, data show a markedly synergic effect of the combination of PEA, in particular PEA-um, and LAC, above all when in association with an antioxidant.

The invention will be now further described by some formulation examples, given by way of exemplary, non-limiting examples of the protection scope of the invention as defined by the appended claims.

Carrageenan (CAR) Test

The carrageenan (CAR) test was performed according to a protocol that provides intra-plantar injection of carrageenan in rats and administration of the active ingredient orally by gavage. This is a standard inflammation test.

The 1% (weight/volume) carrageenan solution (Sigma) was prepared in sterile saline and subsequently kept at 37° C. for 1 hour to obtain complete solubilization. The paw edema was induced in Wistar male rats by injecting 200 µl of carrageenan into the plantar aponeurosis of the right hind paw.

The increase in size of the treated paw was measured prior to induction and 30 minutes after injection of the inflammatory agent using a plethysmometer (model 7140; Ugo Basile). The subsequent paw size measurements were taken at 60-minute intervals with respect to the first measurement, for a total of 7 measurements. The difference between the values obtained from the treated animals and the control animals was calculated and assessed statistically for all six hours.

Hyperalgesic response to heat was measured at various time points (0, 30 min, 1, 2, 3, 4, 5 and 6 h) in accordance with the method described by Hargreaves et al. (Pain, 32 (1988), 77-88) using the Plantar Test 7371 (Ugo Basile, Italy). In short, the animals were allowed to move freely in an open transparent plastic chamber. After a period of acclimatization, a heat source radiating infrared light (IR 60) was placed under the glass floor and concentrated on the hind paw. When the animal felt pain and withdrew its paw, the source was turned off and the time measured was recorded.

An interruption time of 20 sec was set, that is, if the rat did not respond within 20 sec, the test was stopped to prevent the risk of tissue damage.

In the following, PEA-m, PEA-um and PEA-nm stand for "micronized palmitoylethanolamide", "ultra-micronized palmitoylethanolamide" and "non-micronized palmitoylethanolamide", respectively.

Experimental Results

Figure 2A:
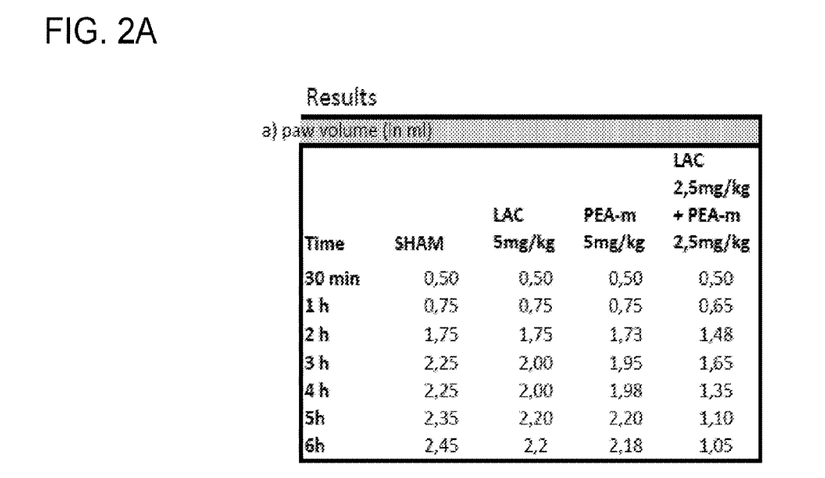
FIGS. 2a) and 2b) show Tables illustrating the data regarding a carrageenan (CAR) test in rats, wherein micronized PEA is used.
Figure 2B:
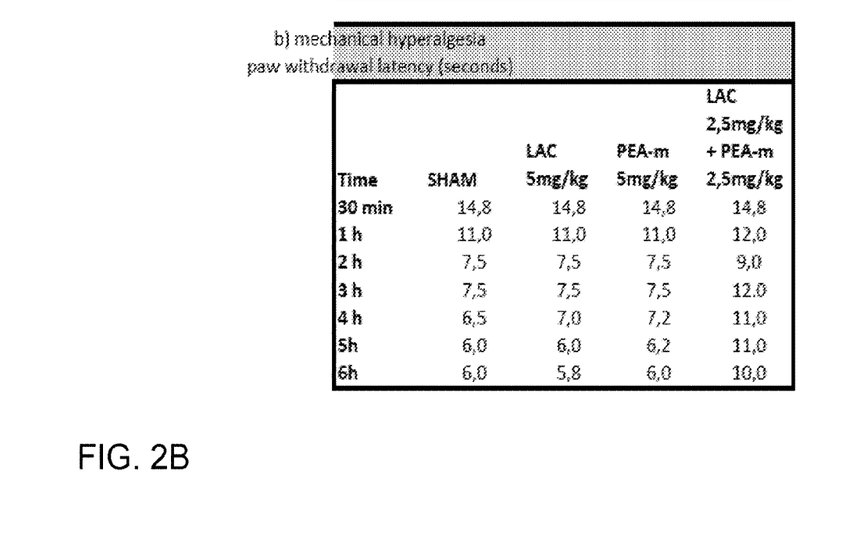

FIG. 2a) and FIG. 2b) show the results regarding the paw volume and paw withdrawal latency time, respectively, after an administration protocol wherein four groups of animals were tested:

1) SHAM, 2) LAC 5 mg/kg, 3) PEA-m 5 mg/kg, 4) LAC 2.5 mg/kg+PEA-m 2.5 mg/kg.

As can be seen from the examination of table a), in the control animals (SHAM) and in those treated with 5 mg/kg of LAC or 5 mg/kg of PEA-m there is a substantial increase in the volume edema from 30 minutes after the carrageenan administration to 6 hours later. Basically then a dose of 5 mg/kg of PEA-m or LAC does not have a significant effect on the formation of the edema by carrageenan (the volume of the paw is only slightly lower than the controls).

Vice versa, by administering half a dose of each active ingredients (2.5 mg/kg for both PEA-m and LAC) but by administering the two active ingredients in combination, in a 1:1 weight ratio, there is an effect of minor growth of the edema which is highly significant (1.05 ml instead of 2.45 ml, compared to an initial volume of 0.50 ml).

Similarly, table b) shows a considerable lengthening of the leg retraction time (10 seconds) by the rat following a mechanical stimulus using a combination of PEA-m+LAC both at a dose of 2.5 mg/kg, i.e. 1:1 weight ratio. Vice versa, doses of 5 mg/kg of PEA-m or individually administered LAC do not show any effect of lengthening the retraction time compared to the control.

The data shown in this preclinical experimentation are clearly indicative of a synergistic effect of the PEA+LAC combination, which is therefore not limited to the combination of ultra-micronized PEA with LAC, nor to the specific weight ratio between the two active ingredients, but which can be generalized.

Figure 3A:
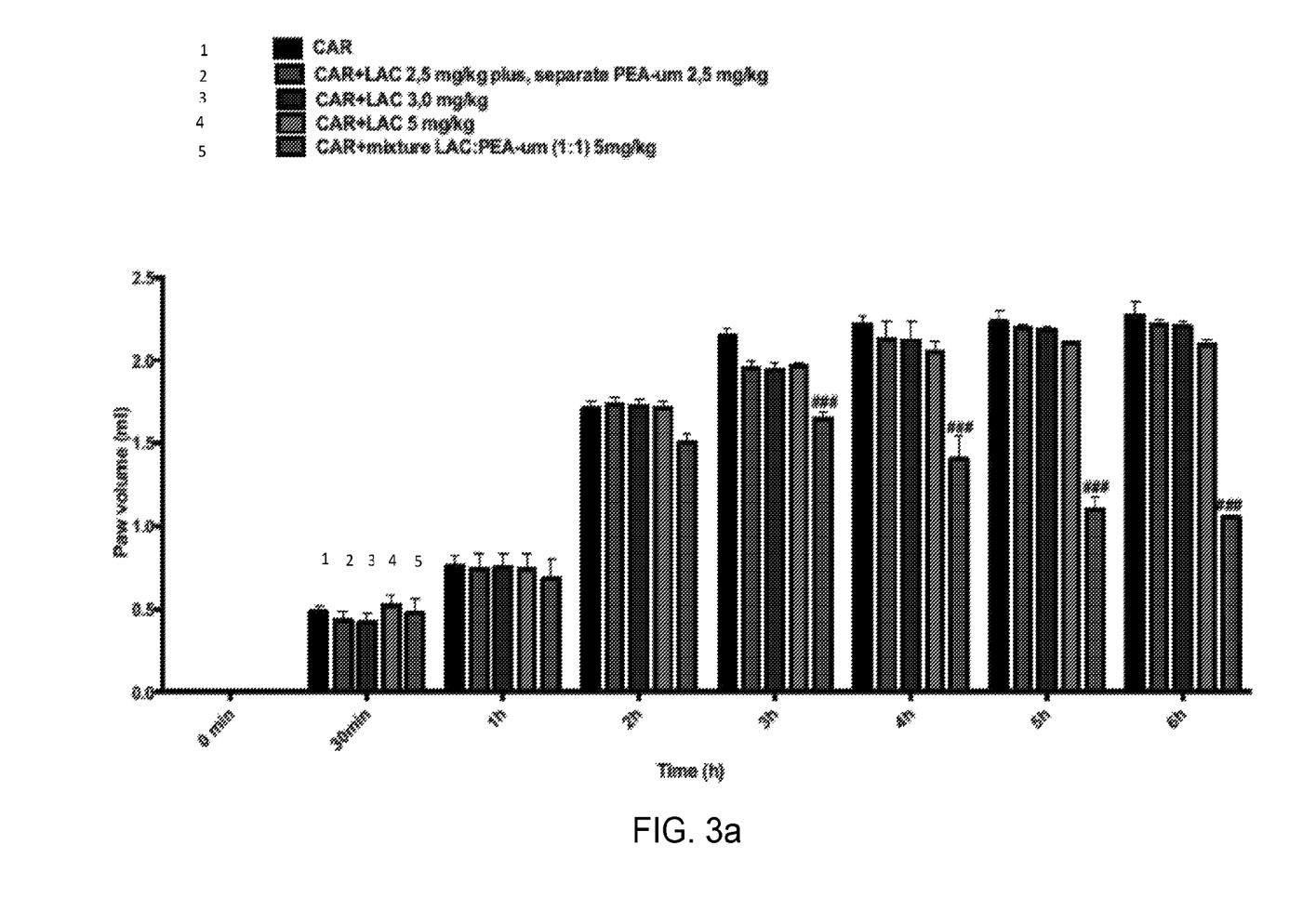
FIGS. 3a) and 3b) show graphs illustrating the data regarding to a carrageenan (CAR) test in rats, wherein a composition (mixture) of ultra-micronized PEA and LAC is compared with separate administration of ultra-micronized PEA and LAC.
Figure 3B:
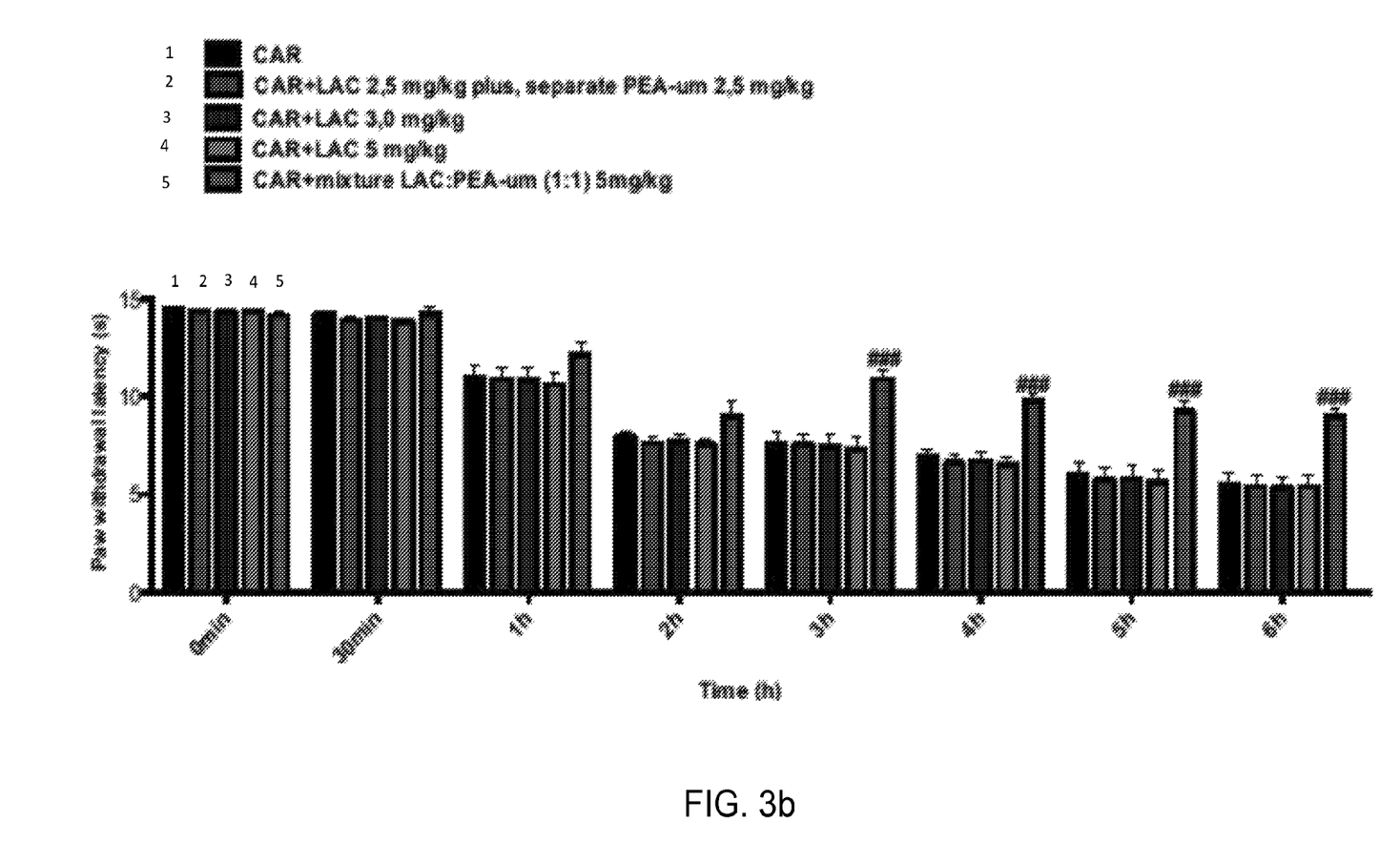

FIG. 3a) and FIG. 3b) show the results of experimental tests performed to compare the administration of a combination PEA+LAC in mixture (pharmaceutical composition) with a separate administration of the two active principles regarding the paw volume and paw withdrawal latency time, respectively.

From this experimentation it is clear that the PEA-um+LAC mixture, in which each one of the two active ingredients is present at a dose of 2.5 mg/kg (i.e. a dose in which the individual components are not active, see the data already contained in FIG. 1), in a weight ratio 1:1, has an activity both on the volume of edema from carrageenan (CAR) and on the mechanical hyperalgesia test, while the separate administration does not differ significantly from the control, as expected according to the data in FIG. 1.

Intraplantar injection of CAR in rats led to a significant increase over time of the volume of the legs. Oral treatment with LAC at a dose of 3.0 mg/kg, 5.0 mg/kg or with LAC at the dose of 2.5 mg/kg plus PEA-um 2.5 mg/kg administered at the same time but as separate compounds, did not achieve a significant reduction in none of the time points. Vice versa, the administration of a suspension in CMC 1.5% (carboxymethylcellulose) of a powder previously dry mixed in a 1:1 ratio (LAC/PEA-um) at the overall dose of 5.0 mg/kg (2.5 mg/kg PEA-um+2.5 mg/kg LAC) significantly reduced the volume of the legs at 3, 4, 5 and 6 h after injection (###P<0.001 vs CAR).

When evaluating the effect on pain, intraplantar injection of CAR in rats led to a significant reduction in the time of latency. Oral treatment with LAC at a dose of 3.0 mg/kg, 5.0 mg kg or with LAC at the dose of 2.5 mg/kg plus PEA-um 2.5 mg/kg administered simultaneously but as separate compounds, did not achieve a significant increase in any of the evaluated time points. Vice versa, the administration of a suspension in 1,5% CMC of a powder previously dry mixed in a 1:1 ratio (LAC/PEA-um) at the overall dosage of 5.0 mg/kg (2.5 mg/kg PEA-um+2.5 mg/kg LAC) significantly increased the latency time at 3, 4, 5 and 6 h after induction of the carrageenan edema (###P<0.001 vs CAR).

Figure 4A:
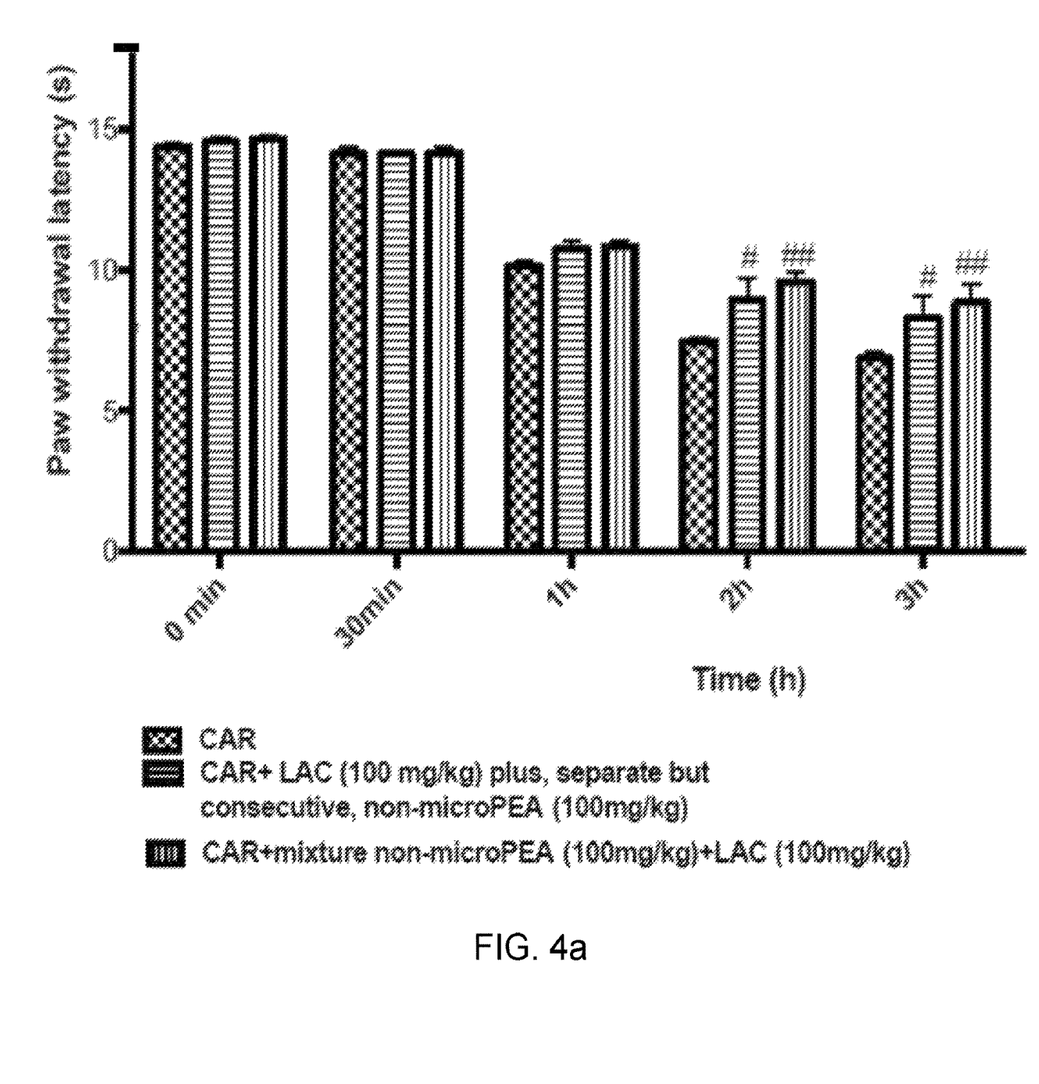
FIGS. 4a) and 4b) show graphs illustrating the data regarding to a carrageenan (CAR) test in rats, wherein a composition (mixture) of non-micronized PEA and LAC is compared with separate administration of non-micronized PEA and LAC.
Figure 4B:
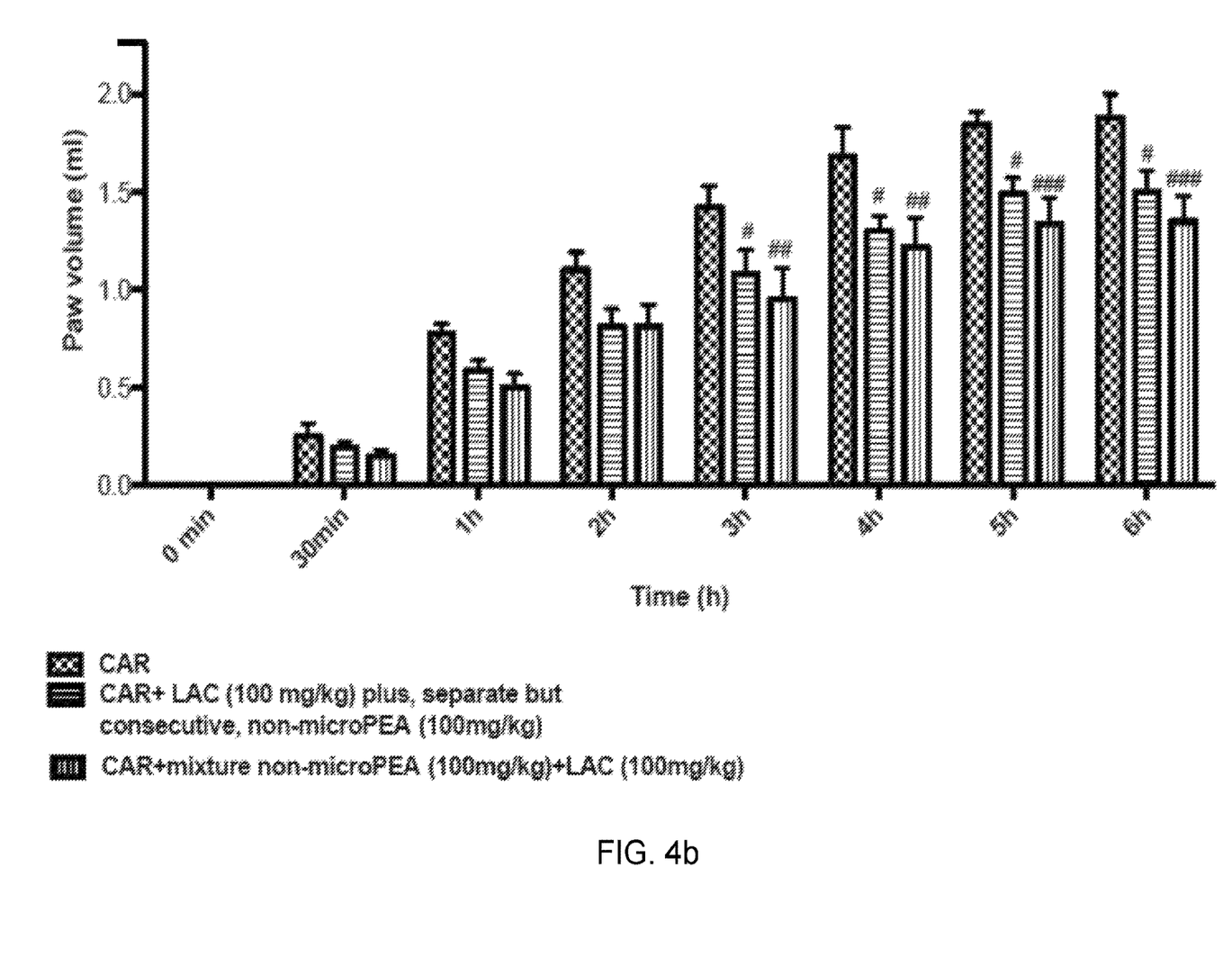

FIG. 4a) and FIG. 4b) show the results of the same experiment of FIGS. 3a)-3b), but using PEA-nm instead of PEA-um at the following doses:
LAC 100 mg/kg plus PEA-nm 100 mg/kg administered simultaneously but as separate compounds;
dry mixture of LAC 100 mg/kg plus PEA-nm 100 mg/kg.

The obtained results clearly show that the combination of PEA-nm and LAC, 1:1 ratio, has a detectable effect after CAR administration when administered as a dry mixture, while the effect of two consecutive administrations of PEA and LAC at the same doses is negligible.

Formulation Examples

Example A—Tablets for Oral Use

Each tablet contains:
150.0 mg PEA-um
300.0 mg LAC
80.0 mg Microcrystalline Cellulose
45.0 mg Croscarmellose Sodium
10.0 mg Polyvinylpyrrolidone
4.0 mg Magnesium Stearate Example B—Tablets for Oral Use Each tablet contains:
200.0 mg PEA-m
300.0 mg LAC
90.0 mg Microcrystalline Cellulose
65.0 mg Croscarmellose Sodium
15.0 mg Polyvinylpyrrolidone
4.0 mg Magnesium Stearate Example C—Tablets for Oral Use Each tablet contains:
200.0 mg PEA-m (co-micronized with Polydatin)
20.0 mg Polydatin (co-micronized with PEA-m)
300.0 mg LAC
90.0 mg Microcrystalline Cellulose
65.0 mg Croscarmellose Sodium
15.0 mg Polyvinylpyrrolidone
4.0 mg Magnesium Stearate Example D—Tablets for Oral Use Each tablet contains:
200.0 mg PEA-m (co-micronized with Quercetin)
25.0 mg Quercetin (co-micronized with PEA-m)
300.0 mg LAC
90.0 mg Microcrystalline Cellulose
65.0 mg Croscarmellose Sodium
15.0 mg Polyvinylpyrrolidone
4.0 mg Magnesium Stearate Example E—Tablets for Oral Use Each tablet contains:
200.0 mg PEA-um
50.0 mg Acetylcysteine
300.0 mg LAC
90.0 mg Microcrystalline Cellulose
65.0 mg Croscarmellose sodium
15.0 mg Polyvinylpyrrolidone
4.0 mg Magnesium Stearate Example F—Tablets for Oral Use Each tablet contains:
150.0 mg PEA-m
100.0 mg (α-Lipoic Acid
200.0 mg LAC
100.0 mg Microcrystalline Cellulose
80.0 mg Croscarmellose sodium
10.0 mg Polyvinylpyrrolidone
5.0 mg Magnesium Stearate Example G—Microgranules for Sublingual Use Each sachet of microgranules contains:
300.0 mg PEA-um
100.0 mg Acetylcysteine
300.0 mg LAC
380.0 mg Sorbitol powder
15.0 mg Saccharose Palmitate
5.0 mg Polysorbate 80 (plant-based).

What is claimed is:
1. A pharmaceutical composition useful in treating neuropathic pain, said pharmaceutical composition comprising: a pharmaceutically effective amount of
a) palmitoylethanolamide (PEA) in a weight percentage of the pharmaceutical composition of between 20 and 35%, b) L-acetylcarnitine (LAC) in a weight percentage of the pharmaceutical composition of between 20 and 55%, and c) a pharmaceutically acceptable excipient, the PEA being in micronized form (PEA-m) with a particle size ranging between 2.0 and 10.0 μm, or in ultra-micronized form (PEA-μm) with a particle size ranging between 0.8 and 6.0 μm, or a mixture thereof, and the pharmaceutical composition being in a form for oral administration.

2. The pharmaceutical composition according to claim 1, wherein the LAC is in pulverized form.

3. The pharmaceutical composition according to claim 1, further comprising a compound having antioxidant activity, wherein the compound having the antioxidant activity is present at a maximum total weight percentage of the pharmaceutical composition of 20%.

4. The pharmaceutical composition according to claim 3, wherein the compound having the antioxidant activity is selected from the group consisting of a polyphenol, alpha-lipoic acid, L-acetylcysteine, and a mixture thereof.

5. The pharmaceutical composition according to claim 4, wherein the compound having the antioxidant activity is a polyphenol selected from the group consisting of polydatin, resveratrol, luteolin, quercetin, rutin, and a mixture thereof.

6. The pharmaceutical composition according to claim 3, wherein the compound having the antioxidant activity is co-micronized with the PEA.

7. The pharmaceutical composition according to claim 1, wherein the PEA and the LAC are present in a combined amount of 10 mg to 1 g.

\* \* \* \* \*